US012745898B2

(12) United States Patent
Buch et al.

(10) Patent No.: US 12,745,898 B2
(45) Date of Patent: Sep. 29, 2026

(54) ENDOSCOPE HANDLE WITH FRAME

(71) Applicant: AMBU A/S, Ballerup (DK)

(72) Inventors: Ken Henrik Buch, Vordingbord (DK); Peter Bender Christoffersen, Kgs. Lyngby (DK); Jonas Hjortlund, Copenhagen S (DK); Charlotte Krag Varslev-Pedersen, Ballerup (DK)

(73) Assignee: AMBU A/S, Ballerup (DK)

( * ) Notice: Subject to any disclaimer, the term of this patent is extended or adjusted under 35 U.S.C. 154(b) by 707 days.

(21) Appl. No.: 18/072,421

(22) Filed: Nov. 30, 2022

(65) Prior Publication Data

US 2023/0165442 A1 Jun. 1, 2023

(30) Foreign Application Priority Data

Dec. 1, 2021 (EP) .................................... 21211782
Dec. 1, 2021 (EP) .................................... 21211783
Feb. 2, 2022 (EP) .................................... 22154689

(51) Int. Cl.

| | |
|---|---|
| ***A61B 1/005*** | (2006.01) |
| ***A61B 1/00*** | (2006.01) |
| ***A61B 1/05*** | (2006.01) |

(52) U.S. Cl.

CPC ........ *A61B 1/0052* (2013.01); *A61B 1/00045* (2013.01); *A61B 1/0011* (2013.01); (Continued)

(58) Field of Classification Search

CPC ............ A61B 1/00066; A61B 1/00105; A61B 1/00114; A61B 1/0052; A61B 1/0053; (Continued)

(56) References Cited

U.S. PATENT DOCUMENTS 3,734,084 A 5/1973 Ousterhout
4,552,129 A 11/1985 Utsugi et al.
(Continued)

FOREIGN PATENT DOCUMENTS

DE 3206381 A1 9/1983
DE 4000410 A1 7/1991
(Continued)

OTHER PUBLICATIONS

Extended search report in European Patent Application No. 22154689.8, dated Jun. 29, 2022, 8 pgs.
(Continued)

*Primary Examiner* — Michael J Carey
*Assistant Examiner* — Stephen Floyd London
(74) *Attorney, Agent, or Firm* — Faegre Drinker Biddle & Reath LLP

(57) ABSTRACT

An endoscope handle for an endoscope for visually inspecting inaccessible places, such as human body cavities, the endoscope handle including: a frame (70) having a first wall portion (101) formed as an integral portion of the frame, the frame being formed as a single component; a liquid-tight chamber (100) accommodating a circuit (25), preferably a printed circuit board, of the endoscope handle, wherein the liquid-tight chamber is at least partly defined by the first wall portion of the frame; and a first shell part (60) and a second shell part (60') together enclosing a cavity (63), the shell parts accommodating and securing the frame within the cavity, the shell parts forming an exterior surface (68) shaped to form an ergonomic grip for an operator, wherein the shell parts and the frame each are formed as separate components.

27 Claims, 11 Drawing Sheets

(52) U.S. Cl.
CPC ........ *A61B 1/00114* (2013.01); *A61B 1/0057* (2013.01); *A61B 1/05* (2013.01)

(58) Field of Classification Search
CPC ......... A61B 1/0057; A61B 1/05; A61B 1/051; A61B 1/053
See application file for complete search history.

(56) References Cited

U.S. PATENT DOCUMENTS

| | | | | |
|---|---|---|---|---|
| 4,685,463 | A | 8/1987 | Williams | |
| 5,169,568 | A | 12/1992 | Ainger, III | |
| 5,347,993 | A | 9/1994 | Tanaka | |
| 5,377,668 | A | 1/1995 | Ehmsen et al. | |
| 6,390,972 | B1 | 5/2002 | Speier et al. | |
| 6,527,707 | B1 | 3/2003 | Frische et al. | |
| 9,622,646 | B2 | 4/2017 | Ouyang et al. | |
| 10,335,020 | B2 | 7/2019 | Oskin | |
| 10,688,284 | B2 | 6/2020 | Hill et al. | |
| 10,758,647 | B2 | 9/2020 | Tobien | |
| 10,905,497 | B2 | 2/2021 | Pandey et al. | |
| 11,103,131 | B2 | 8/2021 | Majima et al. | |
| 11,622,674 | B2 | 4/2023 | Jensen | |
| 11,678,793 | B2 | 6/2023 | Hansen et al. | |
| 11,992,181 | B2 | 5/2024 | Qvist et al. | |
| 2004/0073084 | A1 | 4/2004 | Maeda et al. | |
| 2006/0149127 | A1 | 7/2006 | Seddiqui et al. | |
| 2006/0276690 | A1 | 12/2006 | Farris et al. | |
| 2007/0282167 | A1 | 12/2007 | Barenboym et al. | |
| 2010/0030020 | A1 | 2/2010 | Sanders et al. | |
| 2011/0218400 | A1 | 9/2011 | Ma et al. | |
| 2011/0237891 | A1* | 9/2011 | Sato | G02B 23/2476 600/149 |
| 2013/0190561 | A1 | 7/2013 | Oskin et al. | |
| 2014/0155696 | A1 | 6/2014 | Sakata | |
| 2014/0221749 | A1 | 8/2014 | Grant et al. | |
| 2014/0265313 | A1 | 9/2014 | Durr et al. | |
| 2014/0275763 | A1 | 9/2014 | King et al. | |
| 2014/0336532 | A1 | 11/2014 | Seguy | |
| 2015/0150632 | A1 | 6/2015 | Kappel et al. | |
| 2015/0282701 | A1 | 10/2015 | Oskin et al. | |
| 2016/0367112 | A1 | 12/2016 | Koyama | |
| 2017/0065152 | A1 | 3/2017 | Koyama | |
| 2018/0153381 | A1 | 6/2018 | Wei et al. | |
| 2018/0153389 | A1 | 6/2018 | Dixon et al. | |
| 2018/0296068 | A1 | 10/2018 | Matthison-Hansen et al. | |
| 2018/0296069 | A1 | 10/2018 | Matthison-Hansen | |
| 2018/0303317 | A1 | 10/2018 | Matthison-Hansen | |
| 2018/0303472 | A1 | 10/2018 | Matthison-Hansen et al. | |
| 2018/0309908 | A1* | 10/2018 | Matthison-Hansen | H04N 23/63 |
| 2019/0246877 | A1 | 8/2019 | Mitsuya et al. | |
| 2019/0350440 | A1 | 11/2019 | Leong et al. | |
| 2020/0054194 | A1 | 2/2020 | Melsheimer | |
| 2020/0121304 | A1 | 4/2020 | Johnsen et al. | |
| 2020/0196843 | A1 | 6/2020 | Tah et al. | |
| 2020/0197579 | A1 | 6/2020 | Chu et al. | |
| 2020/0221929 | A1 | 7/2020 | Harada | |
| 2020/0337529 | A1 | 10/2020 | Chu et al. | |
| 2020/0345207 | A1* | 11/2020 | Nguyen | A61B 1/0676 |
| 2021/0068625 | A1 | 3/2021 | Shin et al. | |
| 2021/0100429 | A1* | 4/2021 | Chu | A61B 1/00128 |
| 2021/0137355 | A1 | 5/2021 | Lund et al. | |
| 2021/0203813 | A1 | 7/2021 | Matthison-Hansen et al. | |
| 2021/0298571 | A1 | 9/2021 | Comee et al. | |
| 2022/0160212 | A1* | 5/2022 | Cheon | A61B 1/00105 |
| 2022/0378279 | A1 | 12/2022 | Poll | |
| 2023/0010903 | A1 | 1/2023 | Jen et al. | |
| 2023/0085800 | A1 | 3/2023 | Buch et al. | |
| 2023/0108741 | A1* | 4/2023 | Kawakami | A61B 1/0057 600/146 |
| 2023/0157519 | A1 | 5/2023 | Lund et al. | |
| 2023/0165444 | A1 | 6/2023 | Schtz et al. | |
| 2023/0397799 | A1 | 12/2023 | Nguyen | |
| 2024/0049945 | A1 | 2/2024 | Harris | |
| 2024/0065533 | A1 | 2/2024 | Sharp et al. | |
| 2024/0325682 | A1* | 10/2024 | Hallauer | B29C 66/532 |
| 2024/0374124 | A1* | 11/2024 | Fuchs | A61B 1/0052 |

FOREIGN PATENT DOCUMENTS

| | | | |
|---|---|---|---|
| WO | 2018/162556 | A1 | 9/2018 |
| WO | 2020/123588 | A1 | 6/2020 |
| WO | 2021/213598 | A1 | 10/2021 |

OTHER PUBLICATIONS

Office Action in related U.S. Appl. No. 18/072,383 (1219) dated May 5, 2025, 13 pages.

* cited by examiner

ENDOSCOPE HANDLE WITH FRAME

This application claims priority from and the benefit of European Patent Applications Nos. EP 2215 4689, filed Feb. 2, 2022, EP 2121 1782, filed Dec. 1, 2021, and EP 2121 1783, filed Dec. 1, 2021, said applications incorporated by reference herein in their entirety.

TECHNICAL FIELD

The present disclosure relates to an endoscope handle comprising a frame formed in a single component and a method for assembling such an endoscope handle.

BACKGROUND

Insertion endoscopes are well-known devices in the medical field for visually examining the interior of a hollow organ or cavity of a body, such as lungs or a bladder or intestines, by means of inserting an insertion cord of the endoscope. The insertion cord of the endoscope comprises an elongated insertion tube, a distal tip part, and a bending section connecting the insertion tube with the distal tip part. The endoscope typically has a handle connected to the insertion tube and positioned at the proximal end as seen from the operator. The endoscope further has a vision device, such as a built-in camera (or image sensor) or fibre optics. The vision device is typically incorporated in the distal tip part at the distal end of the endoscope. This definition of proximal as being closest to an operator and distal as being furthest from an operator is used throughout this disclosure. Illumination of the area in front of the distal tip part of the endoscope is normally required, in particular in the field of vision of the vision device. One known way of achieving such illumination is to incorporate one or more Light-Emitting Diodes (LEDs) in the distal tip part of the endoscope. Alternatively, illumination may be provided by light guides and/or fibre optics for guiding light from a light source outside the endoscope and to the distal tip part.

The bending section is provided in order to manoeuvre the endoscope inside the body cavity. The bending section has increased flexibility, e.g. achieved by a number of articulated segments of which the distal tip part forms the distalmost segment. Bending or straightening of the bending section in the insertion part of the endoscope is typically done by tensioning or slacking, respectively, steering wires running from the distal tip part through the remainder of articulated segments and along the inside of the elongated insertion tube to a control device, such as a control lever, of the endoscope handle.

Signal and/or power cables for the vision device (when comprising a camera or image sensor) and other electronics, such as LED lighting accommodated in the distal tip part, also run along the inside of the elongated insertion tube and the bending section from the endoscope handle to the distal tip part. Furthermore, a working channel may run along the inside of the insertion tube and the bending section from the handle to the distal tip part, e.g. allowing liquid to be removed from the body cavity or allowing the insertion of medical tools or surgical instruments into the body cavity. The working channel typically comprises a fluid fitting positioned at the handle and providing access therethrough to a working channel tube extending to an opening in the distal tip of the endoscope.

In some endoscope handles, a circuit is desired to be incorporated in the endoscope handle for example for processing signals or providing power to electronics of a distal end of the endoscope, such as an image sensor. Such a circuit is typically isolated from the environment in the endoscope handle to prevent failures. However, the endoscope handle of prior art solutions is relatively complex to manufacture and assemble. This drawback is especially important when the endoscope handle is employed in a single use or disposable endoscope since the cost of the endoscope can only be borne by a single operation.

Once the functional components of the endoscope handle, e.g. the control device, steering wires, the circuit, and/or the fluid fitting, are enclosed within shell parts of the endoscope handle, it may be difficult to adequately inspect, test, and validate the functions of the endoscope handle. If defects are discovered, then it may be difficult or even impossible to remedy these defects and can therefore result in the entire endoscope handle or even the entire endoscope being discarded. Therefore, there is a need to allow inspection, testing and validation of the functions of the endoscope handle prior to full assembly of the endoscope handle or endoscope. It goes without saying that the performance of the functional components should largely be unaffected by the subsequent assembly of the functional components within the shell parts.

SUMMARY

On this background, it may be seen as an object of the present disclosure to provide an endoscope handle allowing testing of the performance of one or more steering wires attached thereto prior to the complete assembly. Another object of the present disclosure is to provide an endoscope handle involving simplified manufacturing of parts and allowing for a simplified assembly process.

One or more of these objects may be met by aspects of the present disclosure as described in the following.

A first aspect of this disclosure relates to an endoscope handle for an endoscope for visually inspecting inaccessible places, such as human body cavities, the endoscope handle comprising: a frame comprising a first wall portion formed as an integral portion of the frame, the frame being formed as a single component; preferably a liquid-tight chamber accommodating a circuit, preferably a printed circuit board, of the endoscope handle, wherein the liquid-tight chamber is at least partly defined by the first wall portion of the frame; and a first shell part and a second shell part together enclosing a cavity, the shell parts accommodating and securing the frame within the cavity, the shell parts forming an exterior surface shaped to form an ergonomic grip for an operator, wherein the shell parts and the frame each are formed as separate components.

The combination of the first wall portion of the liquid tight chamber and the frame in a single component results in a reduced number of parts to be moulded and a reduced number of parts to be assembled.

In the present disclosure, the frame being formed as a single component may be defined as the frame being formed, e.g. moulded, integrally, i.e. in a single manufacturing process, such as injection moulding, and may be formed or made in a single piece. The frame may be formed of a single material, such as by a single shot injection moulding process, or the frame may be formed of two or more materials, such as by a multi shot injection moulding process.

Additionally or alternatively, the endoscope handle may further comprise a second wall portion, such as a lid, formed separately from the frame. The first wall portion and the second wall portion may together enclose the liquid-tight chamber and may thus form the interior walls of the liquid-tight chamber.

Additionally or alternatively, the first wall portion or preferably the second wall portion may comprise a ledge upon which the circuit is resting.

Additionally or alternatively, the first wall portion and/or the second wall portion may be basin-shaped. The first wall portion and the second wall portion may each enclose approximately half of the volume of the liquid-tight chamber.

Additionally or alternatively, an interface, such as a clearance interface, may be present between the first wall portion and the second wall portion and may be liquid-sealed by a first substance, such as a first sealant. The first substance may preferably fill the clearance interface. The clearance interface may be wedge-shaped.

Additionally or alternatively, the liquid-tight chamber may comprise a liquid-tight port and the endoscope handle may comprise one or more cables in communication with the circuit. The one or more cables may extend through the liquid-tight port. The one or more cables may include: an imaging cable that may be configured for transferring signals and/or power between the circuit and an image sensor of the endoscope, and/or a monitor cable that may be configured for transferring signals and/or power between the circuit and a monitor of an endoscope system, for example a processing unit of the monitor of the endoscope system. The processing unit may be enclosed in a housing of the monitor or may be located separately from the monitor and be in wireless communication with the monitor. In other embodiments, the monitor cable may be omitted and the circuit of the endoscope handle may be in wireless communication with the monitor.

Additionally or alternatively, each cable may comprise one or more wires, which may run in parallel within a jacket of the respective cable. Each wire may be configured for transmitting electrical power or signals and may be in communication with the circuit, such as having an end thereof soldered to the circuit.

Additionally or alternatively, the liquid-tight port may comprise one or more openings in at least one of the first wall portion and the second wall portion. The liquid-tight port may further comprise an entrance compartment leading to the one or more openings. The one or more cables may extend through the entrance compartment and through the one or more openings to the circuit. The entrance compartment may comprise a second substance, such as a second sealant, that may provide a seal around the one or more cables, preferably so as to liquid-seal the one or more openings of the liquid-tight port. The second substance may be the same as or different from the first substance. Further, the entrance compartment may preferably be integrally formed with the frame. The entrance compartment may comprise an aperture for receiving the second substance therethrough.

Additionally or alternatively, the first and second wall portions may be configured so that during filling the entrance chamber with the second substance, the substance also flows into the interface between the first and second wall portions. Thus, first and the second substances may in this case be the same and the actions related to the first substance may thus be performed simultaneously with applying the second substance, i.e. the interface and the entrance compartment may thus be filled simultaneously with the same substance.

Additionally or alternatively, the one or more openings may include an imaging cable opening, optionally formed as a slit, allowing the passage of the imaging cable therethrough and/or a monitor cable opening allowing the passage of the monitor cable therethrough. The area of the monitor cable opening may be larger, preferably at least two times larger, than the area of the imaging cable opening.

Additionally or alternatively, the endoscope handle may further comprise a control device comprising a control lever for being manipulated by an operator. The control device may be at least partly accommodated in the cavity and may be secured to the frame. The control device may be configured for, upon manipulating the control lever, steering a distal end of the endoscope by pivoting about a pivot axis. The frame may comprise at least one channel that may be configured for accommodating a respective wire tube housing a steering wire of the endoscope.

Additionally or alternatively, the at least one channel may be formed as groove(s) in the frame and/or may extend along the longitudinal direction of the frame.

A second aspect of this disclosure relates to an endoscope for visually inspecting inaccessible places, the endoscope comprising: the endoscope handle according to the first aspect of this disclosure; a distal tip part including an image sensor positioned in an interior cavity of the distal tip part; and an insertion tube for insertion into a patient and extending between the endoscope handle and the distal tip part; wherein the image sensor being in signal communication with the circuit of the endoscope handle preferably via an imaging cable through the insertion tube.

Additionally or alternatively, the endoscope may further comprise: a bending section that may include articulated segments connected via hinges and the bending section may be attached to the distal tip part and to the insertion tube; and at least one steering wire that may be attached to a body of the control device of the endoscope handle and may each run through a dedicated wire tube in the insertion cord to the bending section so that manipulating the control device by an operator tensions the at least one steering wire and effects bending of the bending section so as to steer the distal end tip of the endoscope. Such steering wire(s) may function as a so-called Bowden cable.

Additionally or alternatively, each dedicated wire tube may be accommodated in a respective channel that may be formed integrally with the frame. Each channel may comprise a third substance, such as a cured adhesive, that may fix each wire tube in its respective channel.

Additionally or alternatively, each channel may preferably be open. Each channel may preferably further comprise at least one retaining member configured for retaining the wire tube in the channel during installation. The retaining member(s) may preferably locally close the respective channel preferably so that, at the location of the retaining member, the channel fully encloses the respective wire tube.

Additionally or alternatively, the at least one steering wire may include a first steering wire and a second steering wire. The frame may comprise a first channel and a second channel. The channels may preferably be formed integrally with the frame. The first and second channels may extend on opposite sides of the frame, such as on opposite sides of the liquid-tight chamber and may extend along a longitudinal axis of the frame.

Additionally or alternatively, the first and second steering wires may form part of the same steering wire or may be different, separate wires.

A third aspect of this disclosure relates to an endoscope system for visually inspecting inaccessible places, such as human body cavities. The endoscope system comprises: a monitor, and an endoscope comprising endoscope handle according to the first aspect of this disclosure or an endoscope according to the second aspect of this disclosure, wherein the endoscope is connectable to the monitor, preferably via a monitor cable, to establish a signal communication between the monitor and the endoscope. The monitor is configured for displaying an image captured by the image sensor of the distal tip part.

A fourth aspect of this disclosure relates to a method of assembling an endoscope handle, such as an endoscope handle according to the first aspect of this disclosure. The method comprising the steps of: providing: a frame comprising a first wall portion formed as an integral portion of the frame, the frame being formed as a single component, and a first shell part and a second shell part; arranging the frame in one of the shell parts; preferably arranging a circuit, preferably a printed circuit board, at the first wall portion, and liquid sealing the first wall portion to form a liquid-tight chamber defined at least partly by the first wall portion; and closing the first shell part and the second shell part to enclose a cavity and accommodating and securing the frame within the cavity and forming an exterior surface shaped to form an ergonomic grip for an operator.

Additionally or alternatively, the step of providing the frame and the shell parts may further comprise providing a second wall portion, such as a lid, formed separately from the frame. The step of liquid sealing the first wall portion may further comprise arranging the second wall portion adjacent to the first wall portion to form an interface between the first wall portion and the second wall portion; and applying a first substance, such as a first sealant, to liquid seal the interface between first wall portion and the second wall portion, whereby the first wall portion and the second wall portion define the liquid-tight chamber.

Additionally or alternatively, the step of arranging the circuit may be alternatively comprise arranging the circuit on in the second wall portion, preferably on a ledge of the second wall portion, so that the circuit is retained by the second wall portion. Preferably, the method includes a step of establishing electrical communication between each of the one or more cables and the circuit, such as by soldering an end of the one or more cables, e.g. an end of each individual wire of each of the one or more cables, onto the circuit.

Additionally or alternatively, the method may further comprise: inserting one or more cables, such as an imaging cable and/or a monitor cable, in communication with the circuit through a port of the chamber, preferably through one or more openings, such as an imaging cable opening and/or a monitor cable opening, formed in the first wall portion and/or the second wall portion; filling an entrance compartment of the port with a second substance, such as a second sealant, so that the second substance envelops the one or more cables in the entrance compartment; and causing the second substance to or letting the second substance liquid-seal the port, such as by curing the second adhesive, for instance by ultraviolet light, or by letting the second adhesive cure.

Additionally or alternatively, the method may be a method for assembling an endoscope. The endoscope may comprise the endoscope handle. Further, the method may comprise: arranging one or more wire tubes each in a respective channel, which is formed integrally with the frame, each of the one or more wire tubes accommodating a dedicated steering wire that when tensioned, effects bending of a bending section so as to steer a distal end tip of the endoscope; applying a third substance, such as an adhesive, in each channel; and causing or letting the third substance cure, e.g. via exposure to ultraviolet light, so as to fix each wire tube in the respective channel.

Additionally or alternatively, the second wall portion may comprise or consist essentially of a transparent material, such as a transparent polymer material. Further, the first substance and/or the second substance and/or the third substance may be light-curable sealants, such as curable by ultraviolet light.

The following is an item list of exemplary embodiments:

1. An endoscope handle for an endoscope for visually inspecting inaccessible places, such as human body cavities, the endoscope handle comprising:
   a frame (70) comprising a first wall portion (101) formed as an integral portion of the frame, the frame being formed as a single component; and
   a first shell part (60) and a second shell part (60') together enclosing a cavity (63), the shell parts accommodating and securing the frame within the cavity, the shell parts forming an exterior surface (68) shaped to form an ergonomic grip for an operator, wherein the shell parts and the frame each are formed as separate components.
   a control device (80) comprising a control lever (81) for being manipulated by an operator, wherein the control device is at least partly accommodated in the cavity (63) and is secured to the frame, the control device being configured for, upon manipulating the control lever, steering a distal end (50) of the endoscope by pivoting about a pivot axis (P),
   wherein the frame comprises at least one channel (110, 110') accommodating a respective wire tube (23, 23'), the wire tube housing a steering wire (22, 22').
2. An endoscope handle according to item 1, wherein each channel comprises a third substance, such as a cured adhesive, fixing the respective wire tube to the channel.
3. An endoscope handle according to any one of the previous items, wherein the at least one channel is integrally formed with the frame.
4. An endoscope handle according to any one of the previous items, wherein the frame comprises a first channel (110) and a second channel (110'), the channels (110, 110') being formed integrally with the frame, wherein the first and second channels extend on opposite sides of the frame, preferably on opposite sides of a liquid-tight chamber, and along a longitudinal axis (L) of the frame.
5. An endoscope handle according to any one of the previous items further comprising a liquid-tight chamber (100) accommodating a circuit (25), preferably a printed circuit board, of the endoscope handle, wherein the liquid-tight chamber is at least partly defined by the first wall portion of the frame.
6. An endoscope handle according to any one of the previous items, further comprising a second wall portion (101'), such as a lid, formed separately from the frame, wherein the first wall portion and the second wall portion together enclose the liquid-tight chamber.
7. An endoscope handle according to any one of the previous items, wherein an interface (103), such as a clearance interface, between the first wall portion and the second wall portion is liquid-sealed by a first substance (108), such as a first sealant, preferably by the first substance filling the clearance interface.
8. An endoscope handle according to any one of the previous items, the liquid-tight chamber comprises a liquid-tight port (104), wherein the endoscope handle comprises one or more cables (13, 53) in communication with the circuit and extending through the liquid-tight port, the one or more cables including:

an imaging cable (53) configured for transferring signals and/or power between the circuit and an image sensor of the endoscope, and/or a monitor cable (13) configured for transferring signals and/or power between the circuit and a monitor (11) of an endoscope system.

9. An endoscope handle according to item 8, wherein the liquid-tight port comprises one or more openings (105, 106) in at least one of the first wall portion and the second wall portion, and an entrance compartment (107) leading to the one or more openings, wherein the one or more cables extend through the entrance compartment and through the one or more openings to the circuit, and wherein the entrance compartment comprises a second substance (108'), such as a second sealant, providing a seal around the one or more cables so as to liquid-seal the one more openings of the liquid-tight port, wherein the entrance compartment is preferably integrally formed with the frame.

10. An endoscope for visually inspecting inaccessible places, the endoscope comprising:

the endoscope handle (20) according to any one of the previous items;

a distal tip part (50) including an image sensor positioned in an interior cavity of the distal tip part; and an insertion tube (30) for insertion into a patient and extending between the endoscope handle and the distal tip part;

wherein the image sensor being in signal communication with the circuit (25) of the endoscope handle preferably via an imaging cable (53) through the insertion tube.

11. An endoscope according to item 10, wherein the endoscope comprises:

a bending section (40) including articulated segments (41) connected via hinges (42), the bending section being attached to the distal tip part and the insertion tube; and at least one steering wire (22, 22') attached to a body (84) of the control device of the endoscope handle and running through a dedicated wire tube (23, 23') in the insertion cord to the bending section so that manipulating the control device by an operator tensions the at least one steering wire (22) and effects bending of the bending section (40) so as to steer the distal end tip of the endoscope.

12. An endoscope according to item 11, wherein each wire tube (23, 23') is accommodated in a respective channel (110, 110') formed integrally with the frame, wherein each channel comprises a third substance (108"), such as a cured adhesive, fixing each wire tube to its respective channel.

13. An endoscope according to any one of items 11-12, wherein the at least one steering wire includes a first steering wire (22) and a second steering wire (22'), wherein the frame comprises a first channel (110) and a second channel (110'), the channels (110, 110') being formed integrally with the frame, wherein the first and second channel extend on opposite sides of the frame, preferably on opposite sides of the liquid-tight chamber, and along a longitudinal axis (L) of the frame.

14. An endoscope system for visually inspecting inaccessible places, such as human body cavities, the endoscope system comprising:

a monitor (11), and an endoscope (1) comprising endoscope handle (20) according to any one of items 1-9 or an endoscope (1) according to any one of items 10-13, wherein the endoscope is connectable to the monitor, preferably via a monitor cable (13), and the monitor is configured for displaying an image captured by the image sensor of the distal tip part.

15. A method of assembling an endoscope handle (20) according to any one of items 1-9, comprising the steps of:

providing:

a frame (70) comprising a first wall portion (101) formed as an integral portion of the frame, the frame being formed as a single component, and a first shell part (60) and a second shell part (61);

arranging one or more wire tubes (23, 23') each in a respective channel (110, 110') formed integrally with the frame, each of the one or more wire tubes accommodating a dedicated steering wire (22, 22') that, when tensioned, effects bending of a bending section (40) so as to steer a distal end tip (50) of the endoscope (1);

applying a third substance (108") in each channel;

causing or letting the third substance cure so as to fix each wire tube in the respective channel;

arranging the frame in one of the shell parts; and closing the first shell part and the second shell part to enclose a cavity (63) and accommodating and securing the frame within the cavity and forming an exterior surface (68) shaped to form an ergonomic grip for an operator.

16. A method according to item 15 further comprising a step of:

arranging a circuit (25), preferably a printed circuit board, at the first wall portion, and liquid-sealing the first wall portion to form a liquid-tight chamber (100) defined at least partly by the first wall portion.

17. A method according to any one of items 15-16, wherein the step of providing further comprises:

providing a second wall portion (101'), such as a lid, formed separately from the frame, wherein the step of liquid-sealing the first wall portion further comprises:

arranging the second wall portion adjacent to the first wall portion to form an interface (103) between the first wall portion and the second wall portion, and applying a first substance (108) to liquid-seal the interface between first wall portion and the second wall portion, whereby the first wall portion and the second wall portion define the liquid-tight chamber.

18. A method according to any one of items 16-17, further comprising:

inserting one or more cables (53, 13), such as an imaging cable (53) and/or a monitor cable (13), in communication with the circuit through a port (104) of the chamber, preferably through one or more openings, such as an imaging cable opening (106) and/or a monitor cable opening (105), formed in the first wall portion and/or the second wall portion;

filling an entrance compartment (107) of the port with a second substance (108'), such as a second sealant, so that the second substance envelops the one or more cables in the entrance compartment; and causing the second substance to or letting the second substance liquid-seal the port, such as by curing the second adhesive, for instance by ultraviolet light, or by letting the second adhesive cure.

A person skilled in the art will appreciate that any one or more of the above aspects of this disclosure and embodiments thereof may be combined with any one or more of the other aspects of this disclosure and embodiments thereof.

BRIEF DESCRIPTION OF THE DRAWINGS

Embodiments of this disclosure will be described in more detail in the following with regard to the accompanying figures. The figures show one way of implementing the present invention and are not to be construed as being limiting to other possible embodiments falling within the scope of the attached claim set.

DETAILED DESCRIPTION

In the following figure description, the same reference numbers refer to the same elements and may thus not be described in relation to all figures. Further, a prime symbol is suffixed for each ordinal element, i.e. a first element is denoted without a prime symbol (for example 100), a second element of the same type is denoted with a single prime symbol (for example 100'), and a third element of the same type is denoted with two prime symbols (for example 100") and so on.

Figure 1:
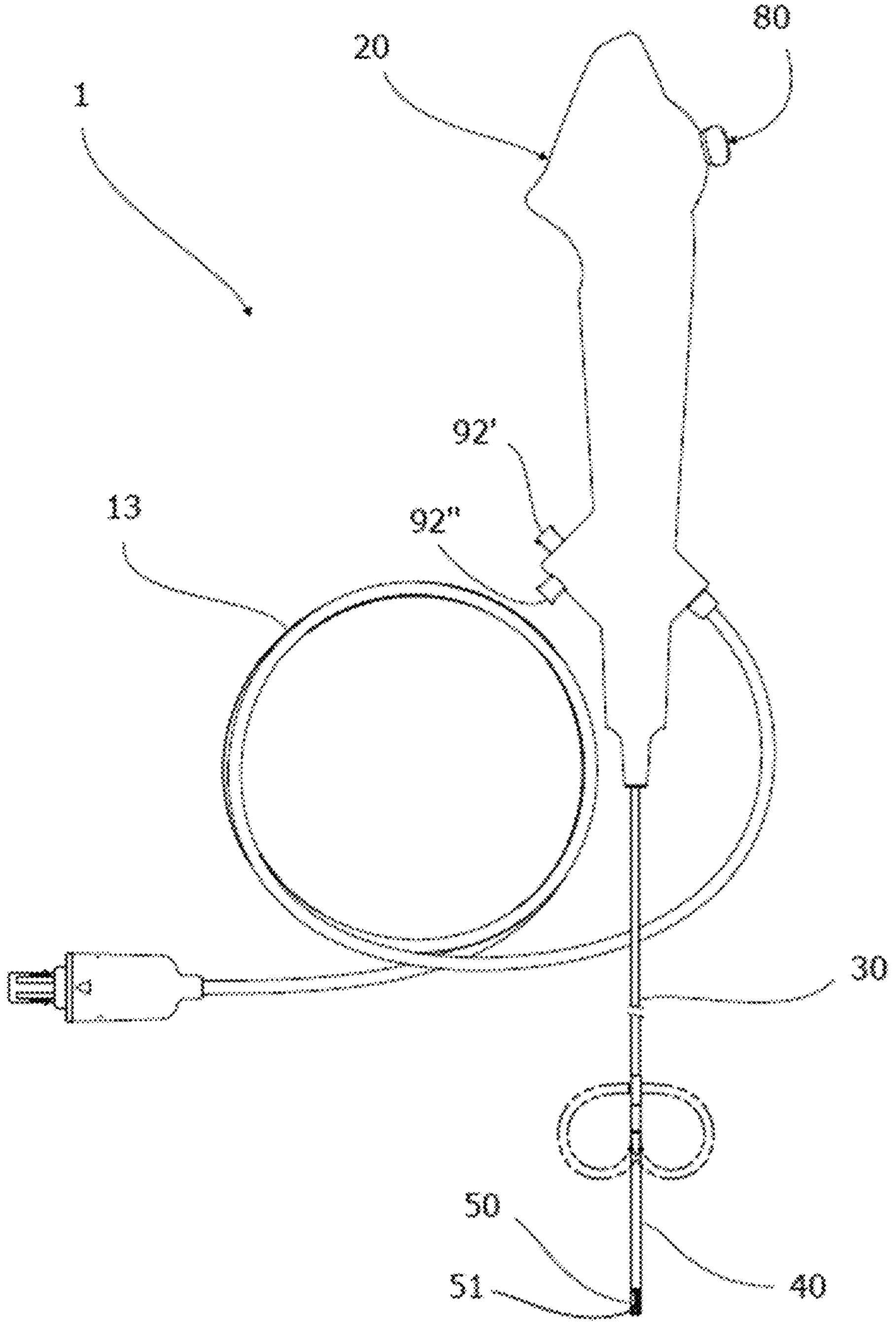
FIG. 1 is a schematics side view of an endoscope illustrating bending of a distal end of the endoscope.
Figure 3:
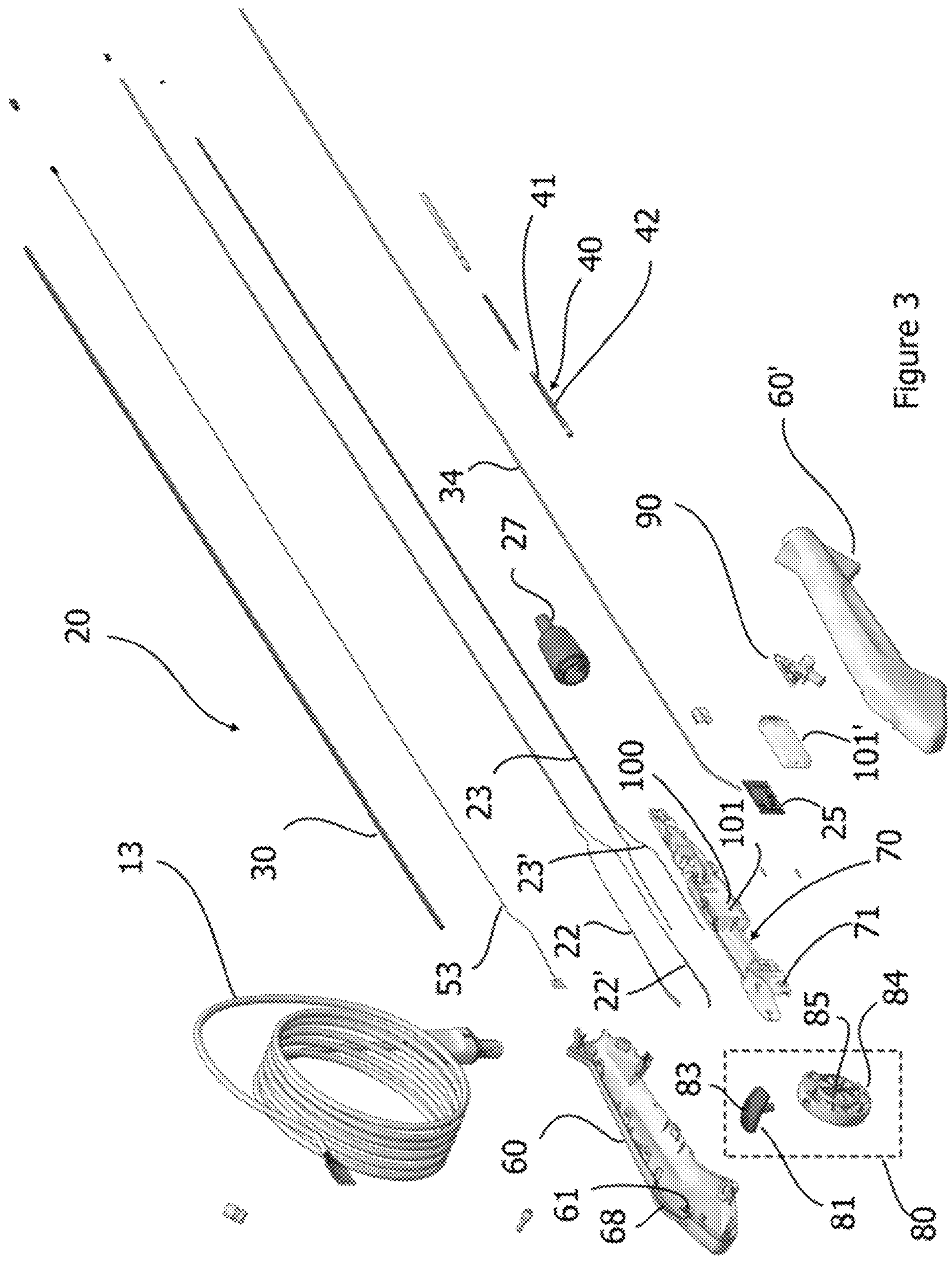
FIG. 3 is schematic exploded view of an endoscope.

FIG. 1 illustrates an endoscope 1, which is disposable and not intended to be cleaned and reused. The endoscope 1 comprises a distal tip part 50, a handle 20 for gripping with a control device, or steering actuator, 80, an insertion tube 30 for insertion into a patient, and a bending section 40. The bending section 40 comprises articulated segments connected by living hinge members as shown in FIG. 3 and is typically formed in one piece by injection moulding. The bending section 40 is connected between the distal tip part 50 and the insertion tube 30. The insertion tube 30 extends between the handle 20 and the bending section 40. The insertion tube 30 has an exterior tubular surface facing the surroundings of the endoscope 1. The distal tip part 50 includes an image sensor 51 positioned in an interior cavity (not shown) of the distal tip part 50.

Figure 2:
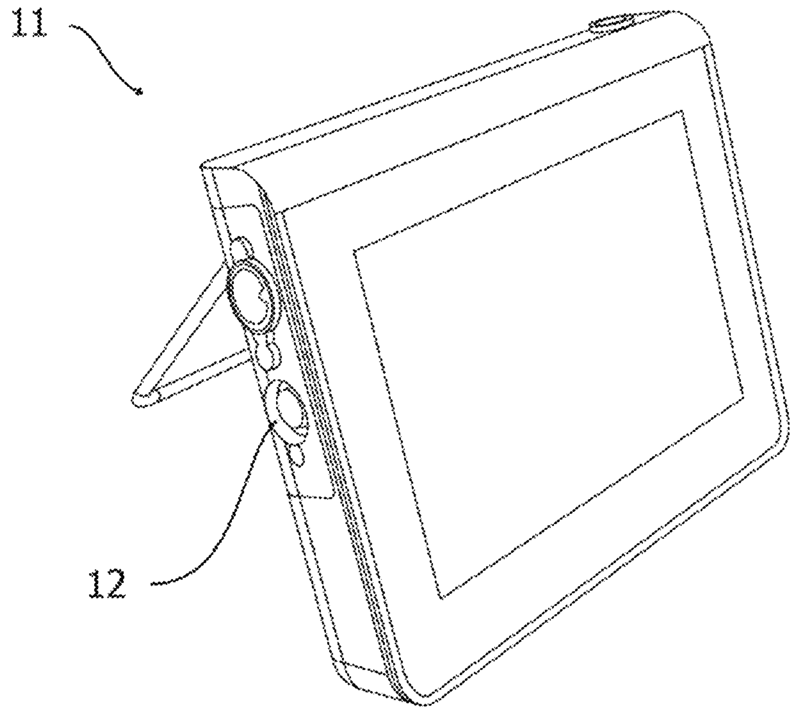
FIG. 2 is a schematic perspective view of a monitor for connecting to the endoscope of FIG. 1.
Figure 9A:
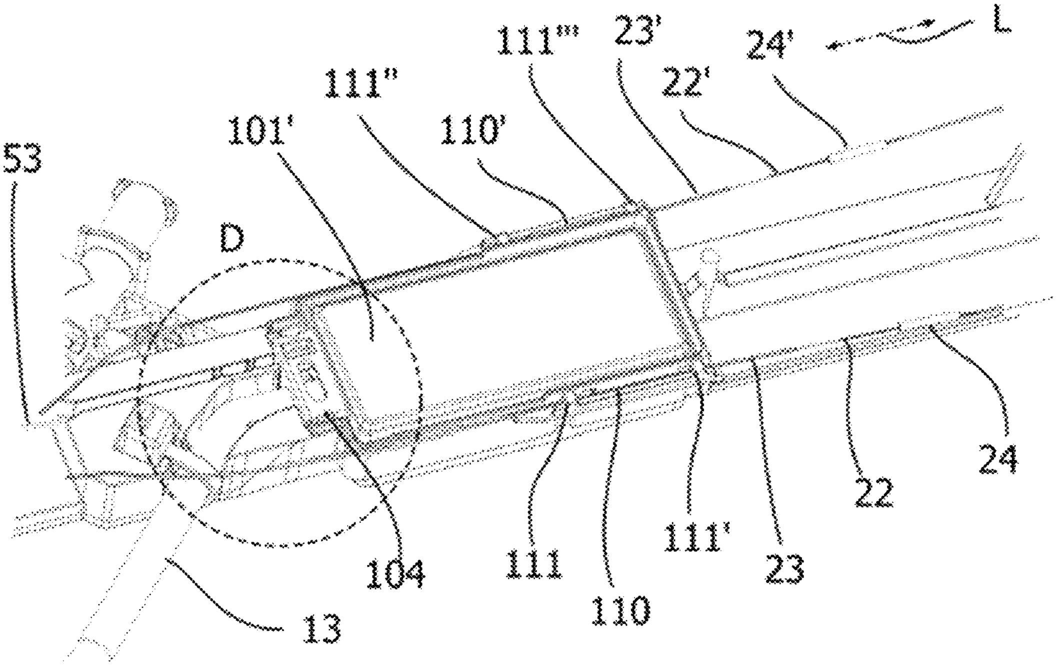
FIG. 9*a* is the same view as FIG. 8*a*, but wherein the second wall portion, the circuit and the cables are shown.

In FIG. 2, a monitor 11 is shown. The monitor 11 comprises a cable socket 12 to which a monitor cable 13 of the endoscope 1 (shown in FIG. 1) can be connected to establish signal communication between the image sensor of the distal tip part 50 and the monitor 11 via a circuit 25 of the handle 20 (shown in FIGS. 3 and 9). The monitor 11 displays images and/or video captured by the image sensor of the endoscope 1, thus allowing an operator to "see" the body cavity through the image sensor of the endoscope 1.

Figure 10A:
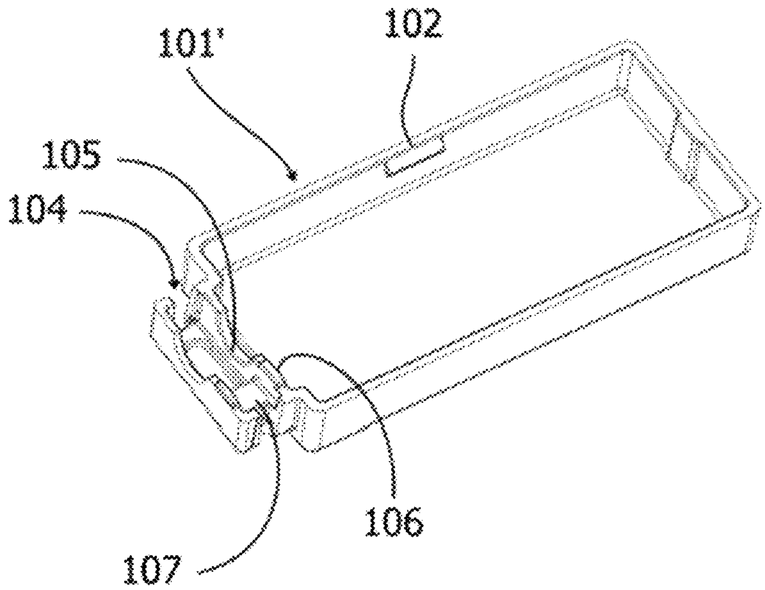
FIG. 10*a* is a perspective view of the second wall portion alone.

Turning to FIG. 3, the components of the endoscope 1 are shown in greater detail in an exploded view. The endoscope handle 20 comprises a first shell part 60, a second shell part 60', a frame 70 comprising an elongate frame body 70', and the steering actuator 80. Two steering wires 22, 22' each extend from the steering actuator 80 through a respective wire tube 23, 23' running through the insertion tube 30 and, optionally, the bending section 40. In one variation, the steering wires 22, 22' are portions of a single wire and are connected to each other by an intermediate portion, or wire loop (not shown), located between the bending section 40 and the distal tip part 50. In another variation, the steering wires 22, 22' are separate wires, each having a distal portion connected to the bending section 40 and/or the distal tip part 50 and a portion accommodated in the wire tube. A working channel extends inside a working channel tube 34 that runs along the inside of the insertion tube 30 and the bending section 40 from fluid openings 92', 92" of a fluid handling device 90 to a distal opening (not shown) in the distal tip part 50. The working channel allows liquid or air to be added to and/or removed from the body cavity or allows for insertion of medical tools or surgical instruments into the body cavity. The frame 70 comprises a chamber 100 defined by a first wall portion 101 formed integrally with the frame 70 and by a second wall portion 101' in the form of a lid (best seen in FIG. 10*a*). A circuit 25 in the form of a printed circuit board is accommodated in the chamber 100, which is then sealed to become liquid-tight. An imaging cable 53 establishes a signal communication between the image sensor (not shown) of the distal tip part 50 and the circuit 25.

Figure 4A:
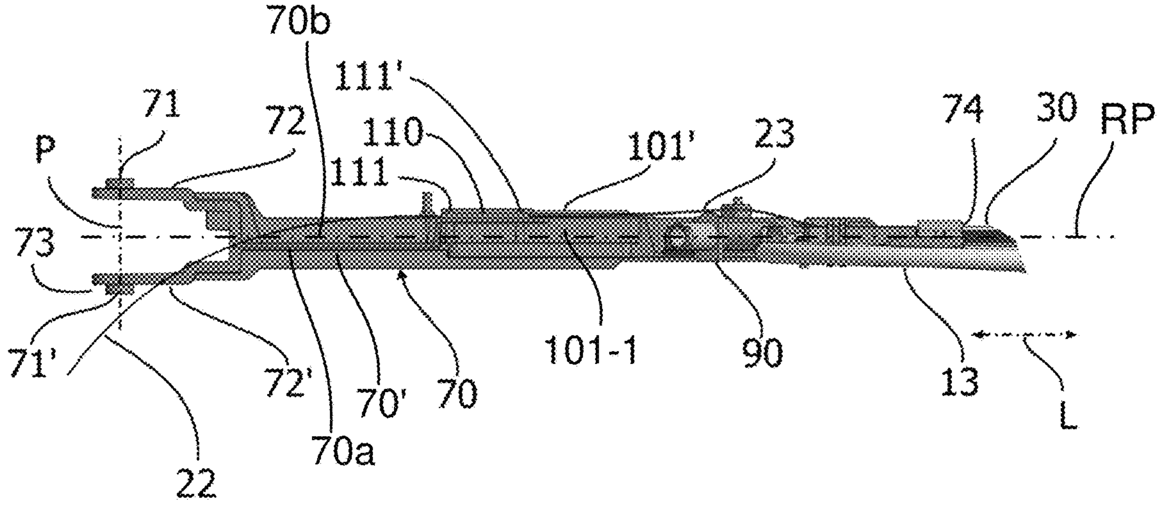
FIG. 4*a* is a top view of a frame of an endoscope handle of the endoscope of FIG. 3.
Figure 4B:
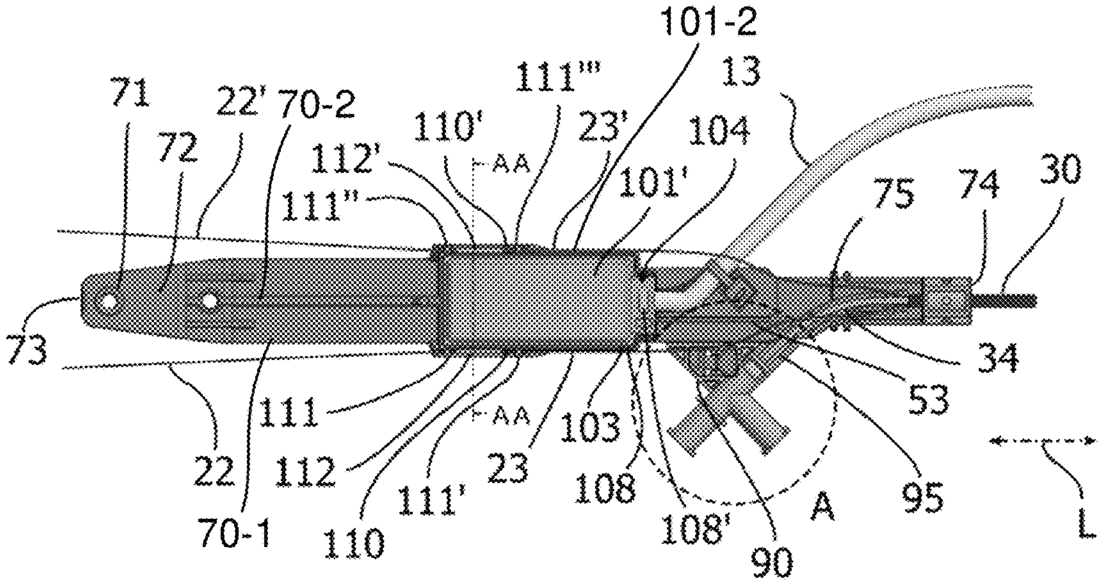
FIG. 4*b* is a side view of the frame of FIG. 4*a*.
Figure 4C:
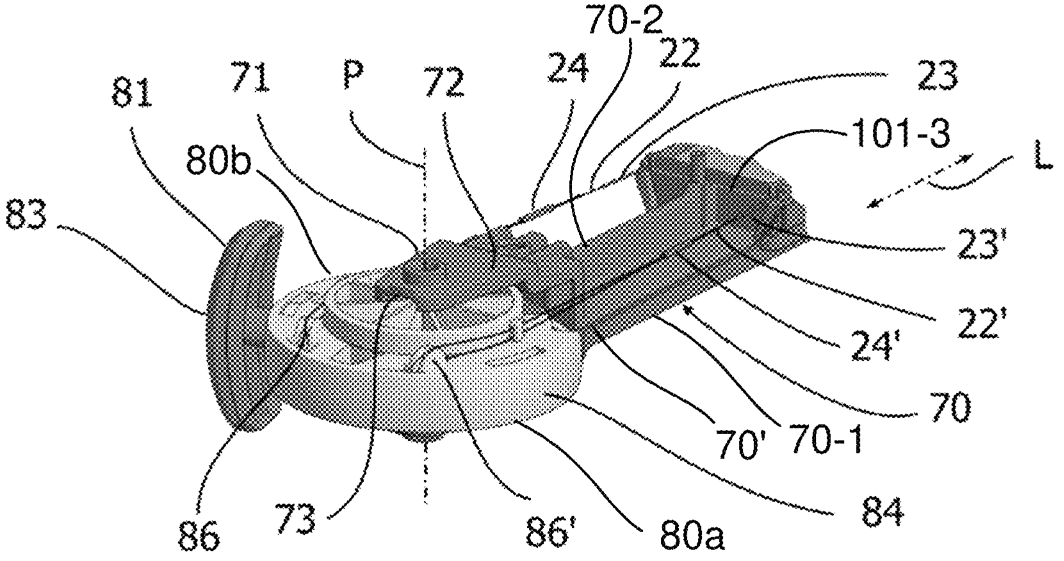
FIG. 4*c* is a schematic perspective view of the frame of FIGS. 4*a* and 4*b* with a mounted control device and steering wires.

Turning to FIGS. 4*a*-4*c*, the details of the frame 70, the steering actuator or control device 80, and the fluid handling device 90 are shown.

As best seen in FIGS. 4*a*-4*b*, the frame 70 comprises the frame body 70' that extends along a longitudinal axis L between a proximal end 73 and a distal end 74. The frame 70 comprises a first bearing 71, as shown in FIGS. 4*a*-4*c*, and a second bearing 71', as shown in FIG. 4*a*. The frame 70 and the bearings 71, 71' are formed in a single piece of a polymer material, preferably by injection moulding. The frame body 70' comprises a first wall portion 101 protruding from a main wall 70-1 of the frame body 70' and traversing a rotation plane RP between the proximal end and the distal end, the bearings receiving the trunnions and rotatably supporting the steering actuator 80. The first wall portion 101 comprises two longitudinal walls 101-1 and 101-2, and comprises a proximal wall 101-3 and a distal wall 101-4, which are connected to the longitudinal walls 101-1 and 101-2 to define a spacing 100-2 (FIG. 5*b*) of the chamber 100. The spacing 100-2 extends transversely between the cover 101' and a base 100-1 provided by the main wall 70-1 of the frame body 70'. The main wall 70-1 separates a first side 70*a* of the frame 70 from a second side 70*b*. A support wall 70-2 extends orthogonally from the main wall 70-1 on the second side 70*b* and extends distally to the proximal wall 101-3. As shown in FIG. 4*b*, the chamber 100 is closed by placing the second wall portion, or lid, 101' on the frame 70.

As best seen in FIG. 4*c*, the control device 80 is arranged at the proximal end 73 of the frame body 70' and comprises a cylindrical body 84 with trunnions 85, 85' (visible in FIG. 5*b* and in particular in FIG. 5*d*), and a control lever 81. The trunnions 85, 85' extend from opposite sides of the body 84 along a pivot axis P. The first trunnion 85 extends from a first side 80*a* of the steering actuator and a second trunnion 85' extends from a second side 80*b* of the steering actuator 80. The rotation plane RP traverses the steering actuator 80 between the first side and the second side and between the trunnions. The control lever 81 has an exterior friction-inducing surface 83 for securely engaging with a finger of an operator so as to allow the operator to pivot the control device 80 about the pivot axis P. FIG. 4*c* also shows a proximal wall 101-3 of the first wall portion 101.

As seen in FIG. 4*c*, the ends of the two steering wires 22, 22' are guided around respective wire loop portions 86, 86' of the body 84 and crimped onto the same steering wire 22, 22' via crimps 24, 24' so as to fix the steering wires 22, 22' to the control device. Since the steering wires run inside wire tubes 23, 23' which are fixed to channels 110, 110' of frame 70 (described in greater details in connection with FIGS. 8*a*, 8*b*, 9*a*, 9*b*, 10*a* and 10*b*), the control device 80 can thus steer the distal tip part 50 of the endoscope when an operator manipulates the friction-inducing surface 83 of the control lever 81 to pivot the control device 80 about the pivot axis P and thus tension one of the steering wires 22, 22'. This principle may be known as a Bowden cable.

The steering wires 22, 22', the working channel tube 34, the imaging cable 53 run along the inside of the bending section 40 and further inside the insertion tube 30, which terminates at its proximal end (i.e. at the handle 20) in an end cap 27. The end cap 27 is arranged about the distal longitudinal end 74 of the frame 70.

Figure 5A:
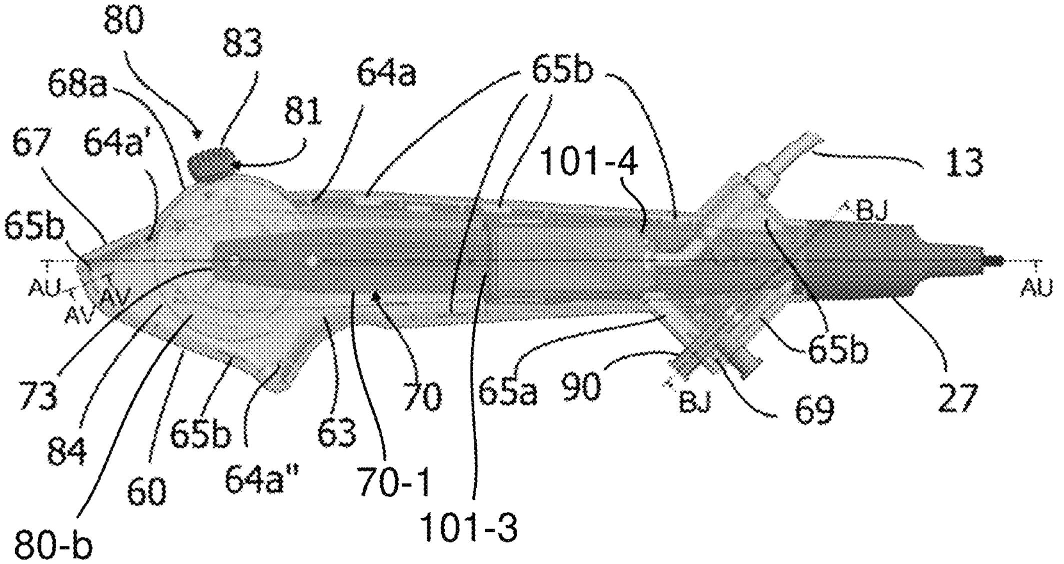
FIG. 5*a* is a schematic side view of an endoscope handle of the endoscope of FIG. 3 shown, wherein the second shell part is omitted to show the interior of the endoscope handle.

The frame further comprises a first arm 72 having the first bearing 71, and a second arm 72' having the second bearing 71'. The arms 72, 72' extend substantially in parallel. The arms 72, 72' comprise respective ramps 77, 77' oriented along the longitudinal axis L and leading to the bearings 71, 71', as best seen in FIG. 5*d*. Further, the arms 72, 72' are configured, when inserting the trunnions 85, 85' in the ramps 77, 77', to flex away from each other to allow insertion of the trunnions 85, 85' in the bearings 71, 71', and to return to a resting position once the trunnions 85, 85' of the control device 80 are arranged in bearings 71, 71' so as to securely hold the trunnions 85, 85' in the bearings 71, 71', and accordingly mount the control device 80 to the frame 70.

Figure 5B:
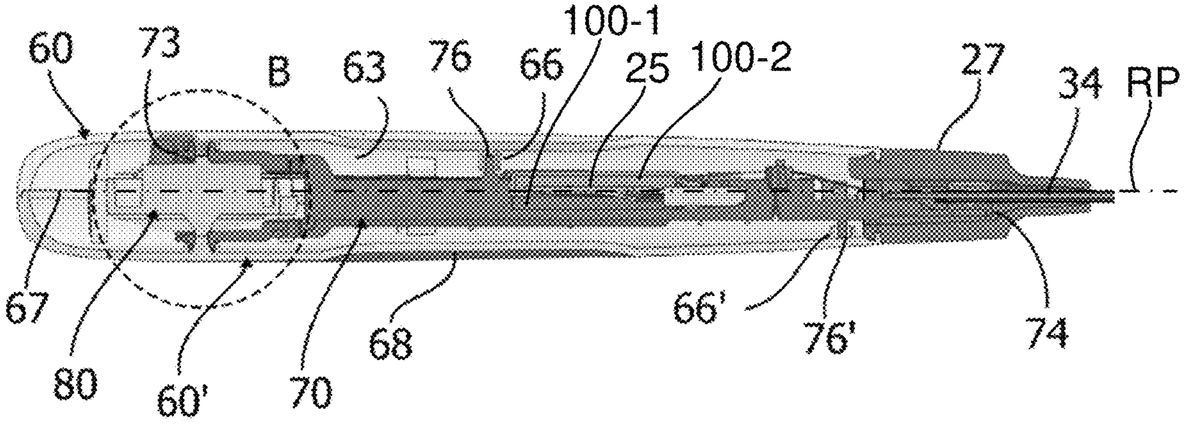
FIG. 5*b* is a cross-sectional view of the endoscope handle along line AU-AU shown in FIG. 5*a*.
Figure 5C:
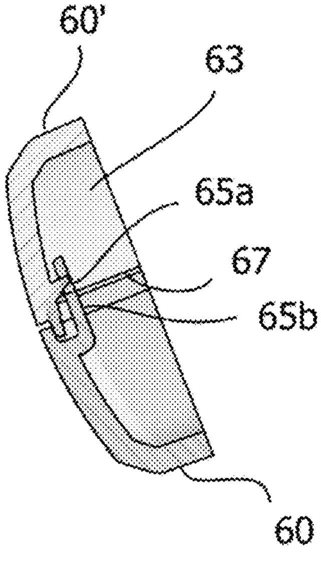
FIG. 5*c* is a cross-sectional view of a snap lock connection of the shell parts along line AV-AV shown in FIG. 5*a*
Figure 5D:
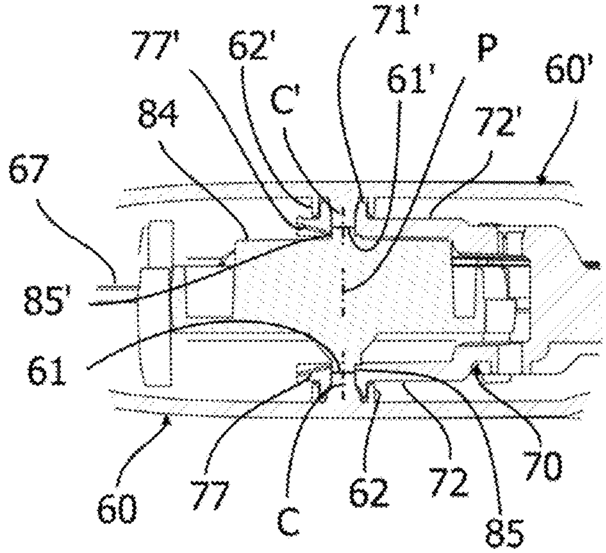
FIG. 5*d* is a detail view of the connection between the shell parts and the control device, as indicated by the dashed circle B shown in FIG. 5*b*.

The first shell part 60 comprises a first column 61, see FIGS. 3, 5*b*, and 5*d*. The second shell part 60' comprises a second column 61', see FIGS. 5*b* and 5*d*. Turning specifically to FIG. 5*d*, the columns 61, 61' extend along a respective column axis C, C' and into the cavity 63 from opposite sides.

The first shell part 60 comprises three first alignment parts 64*a*, 64*a'*, 64*a"*, as best seen in FIG. 5*a*, forming three alignment pairs together with three corresponding second alignment parts (not shown) of the second shell part 60'. The alignment pairs are configured, upon closure of the shell parts, to align the column axes C, C' with respect to each other, and thus the alignment pairs are arranged substantially along the separation line 67 of the shell parts 60, 60' and circumscribe the body 84 of the control device 80, as indicated by the first alignment parts 64*a*, 64*a'*, 64*a"* in FIG. 5*a*.

Figure 6A:
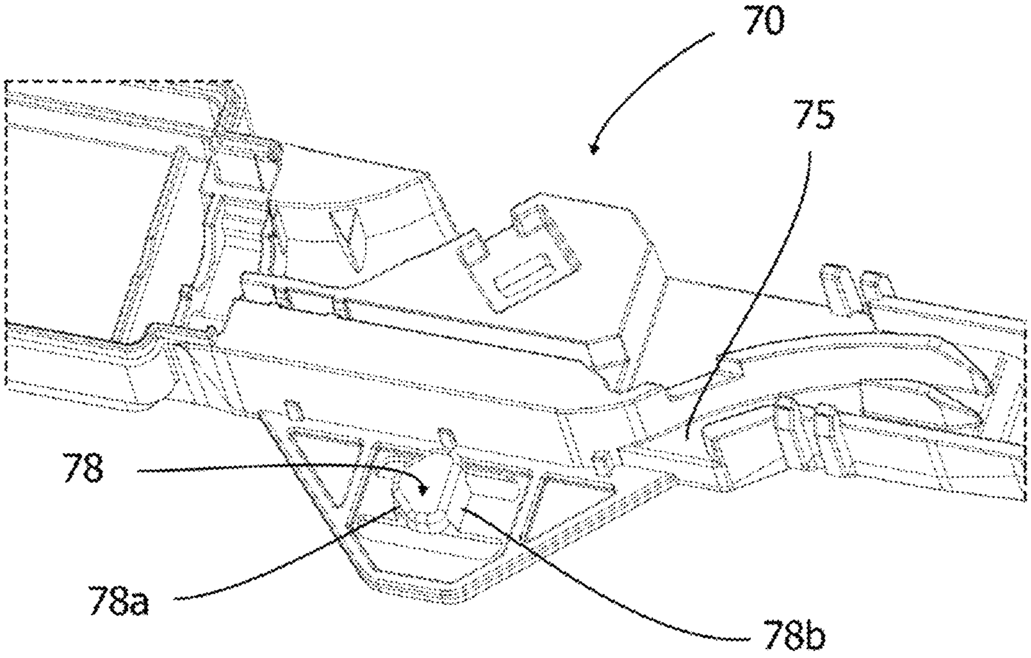
FIG. 6*a* is a detail view at the location of the pin of the frame.
Figure 6B:
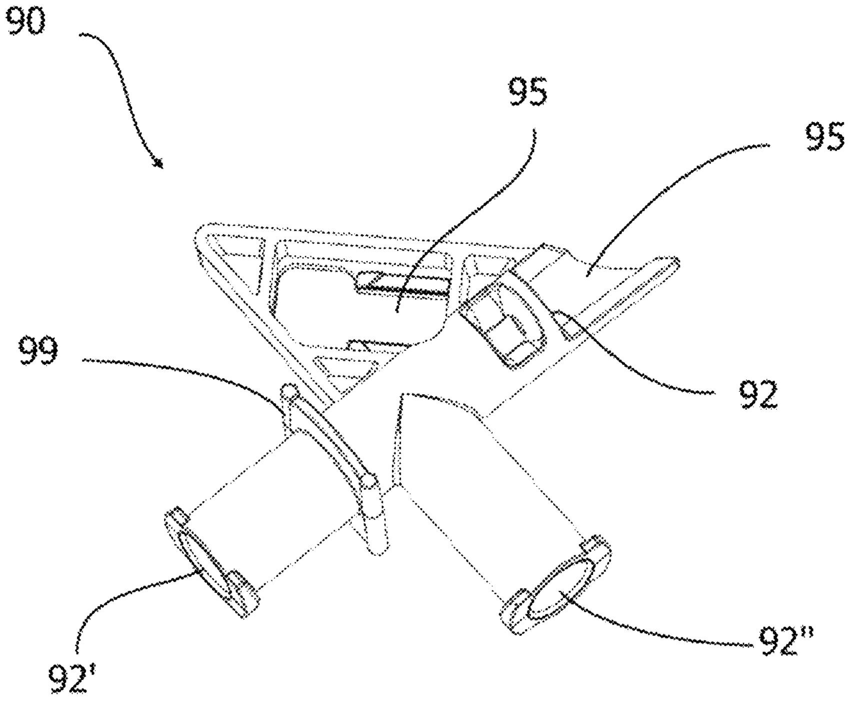
FIG. 6*b* is a perspective view of the fluid handling device.
Figure 7A:
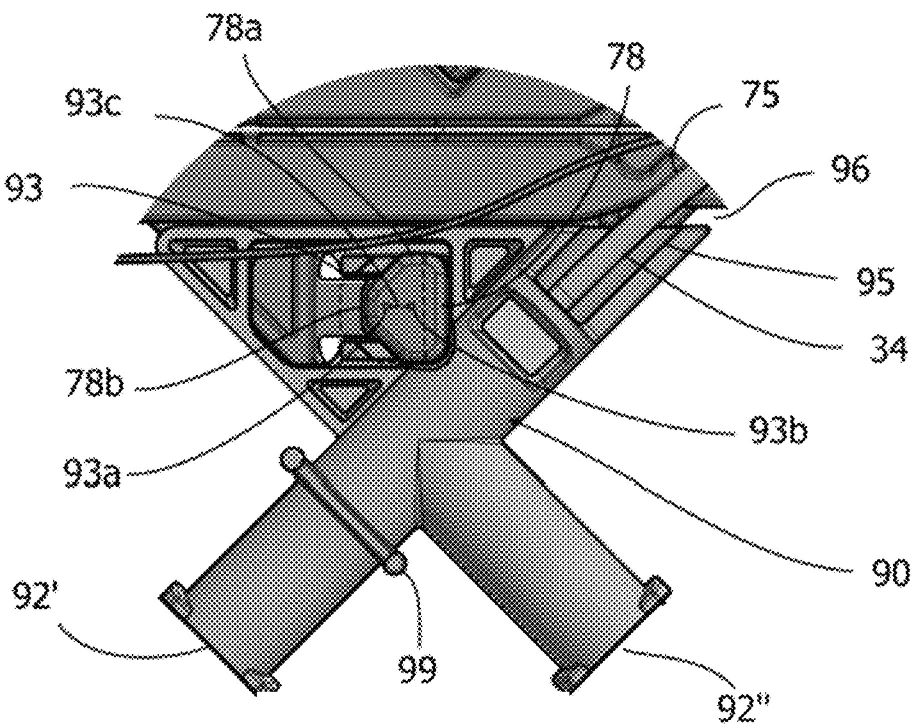
FIG. 7*a* is a detail view of connection between the fluid handling device and the frame, as indicated by the dashed circle A shown in FIG. 4*b*.
Figure 7B:
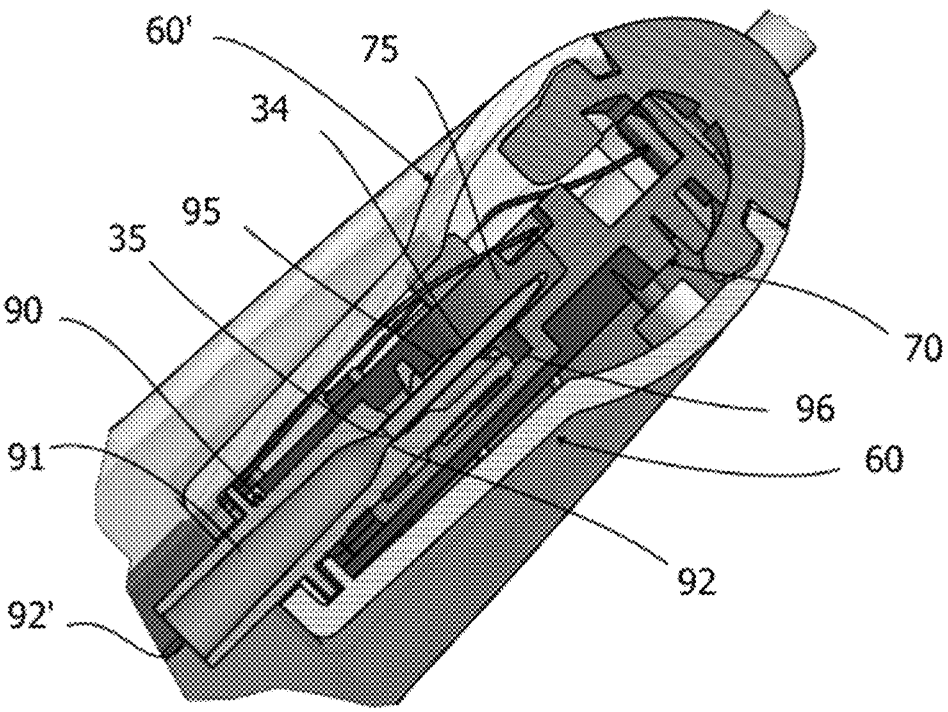
FIG. 7*b* is a cross-sectional view of the connection between the fluid handling device and the tube along line BJ-BJ shown in FIG. 5*a*.

The endoscope handle 20 further comprises a fluid handling device 90 in the form of a T-connector fluid fitting, as best seen in FIGS. 4*b*, 6*b* and 7*a*, which is formed separately from the frame 70. The fluid handling device is arranged substantially at the distal longitudinal end 74 of the frame 70. In other words, the control device 80 and the fluid handling device 90 are arranged at opposite longitudinal ends of the frame 70. As best seen in FIG. 7*b*, the fluid handling device comprises a fluid passage 91 having a first fluid opening 92 and further a second fluid opening 92', and a third fluid opening 92", as shown in FIGS. 6*b* and 7*a*. A proximal opening 35 of the working channel tube 34 is arranged in the first fluid opening 92 and is in fluid communication with the second fluid opening 92' and the third fluid opening 92".

The fluid handling device 90 is securely mounted onto the frame 70 via an interface in the form of a prismatic joint comprising a slot 93 and a pin 78 secured to the slot 93. In this embodiment, the slot 93 forms part of the fluid handling device 90, as shown in FIG. 6*b*, and the pin 78 forms part of the frame 70, as shown in FIG. 6*a*, but may in other embodiments be vice versa.

The pin 78 comprises a body 78*b* extending along a pin direction (through the plane of FIG. 7*a*) and a head 78*a*. As best seen in FIG. 6*a*, the body 78*b* is accommodated in the slot 93 and terminates in the head 78*a*, which secures the pin 78 to the slot 93 by preventing removal of the pin along the pin direction.

The slot 93 defines a pre-determined path extending along the longitudinal axis L between a proximal end position 93*a* of the slot 93, which is closest to the proximal longitudinal end 73 of the frame 70, and a distal end position 93*b* of the slot 93, which is farthest from the proximal longitudinal end 73 of the frame 70.

In the arrangement shown in FIGS. 4*a*-4*b*, i.e. prior to assembly with the shell parts 60, 60', the interface permits translational movement of the pin 78 in the slot 93 between the proximal end position 93*a* of the slot 93 and the distal end position 93*b* of the slot 93. The distance between the proximal end position 93*a* and the distal end position 93*b* is in the range of 0.2 mm to 2.5 mm, preferably around 1.25 mm, as this has been found to allow movement to absorb typical dimensional variation. However, the distance may be even less or more in some embodiments. Further, the working channel tube 34 is arranged with enough slack to allow movement of the fluid handling device 90 relative to the frame 70 via the interface.

As best seen in FIGS. 4*b*, 7*a*, and 7*b*, the frame 70 comprises a first tube guide passage 75 accommodating the working channel tube 34 and guiding the tube 34 towards the second longitudinal end 74 of the frame 70 (see FIG. 4*b*) and towards the first fluid opening 92 (see FIG. 7*b*). The fluid handling device 90 comprises a second tube guide passage 95 that accommodates the tube 34 and guides the tube 34 from the first fluid opening 92 and towards the first tube guide passage 75. The first tube guide passage 75 and the second tube guide passage 95 are separated by a gap 96, as best seen in FIGS. 7*a*-7*b*. The tube guide passages 75, 95 are formed as open channels having a channel bottom and two opposing channel walls and an open top side providing access to the channel. This allows the assembler to fit the tube 34 within the tube guide passages 75, 95 through the open top side.

The frame comprises two first engagement portions 76, 76' interlocking with two corresponding second engagement portions 66, 66' of the shell parts 60, 60', as best seen in FIG. 5*b*. The bearings 71, 71' also function as two further first engagement portions, and the collars 62, 62' also function as two further corresponding second engagement portions. The corresponding first and second engagement portions are configured, upon closure of the shell parts 60, 60', to engage and fix the frame 70 within the shell parts 60, 60'.

The shell parts 60, 61' comprise nine snap lock pairs. Each pair includes a male part 65*a* of one of the shell parts 60, 60' and a corresponding female part 65*b* of another one of the shell parts 60, 60'. The snap lock pairs are configured to be engaged, upon closure of the shell parts 60, 60', to fix the shell parts to each other.

Figure 8A:
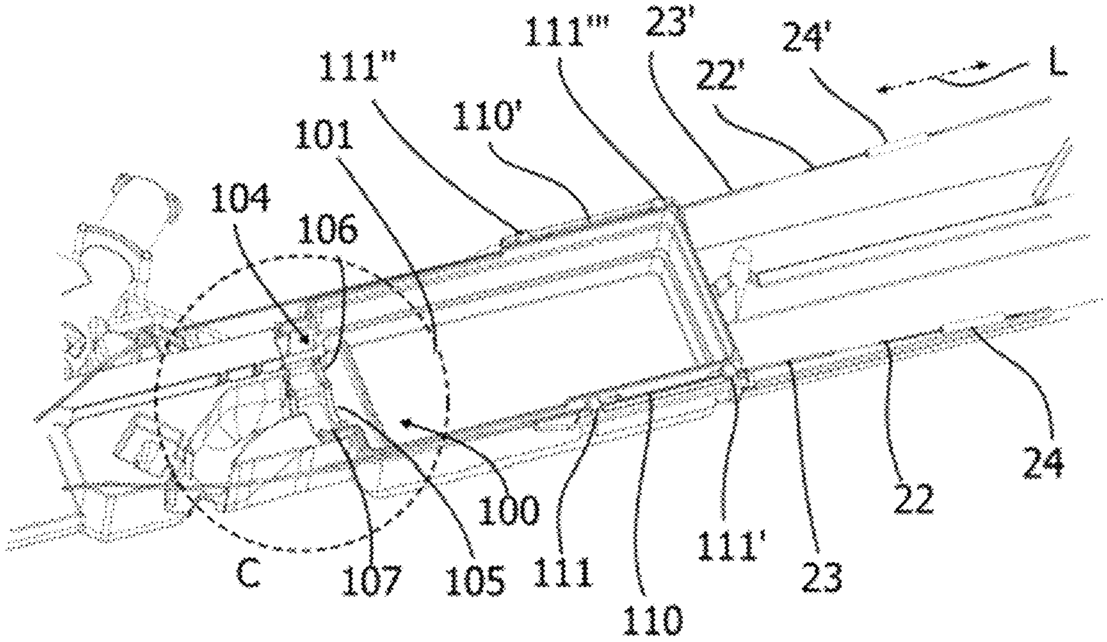
FIG. 8*a* is a detail perspective view of the central part of the frame shown in FIG. 4*b* that includes the liquid-tight chamber, but with the second wall portion, the circuit and the cables omitted for visualisation purposes.
Figure 8B:
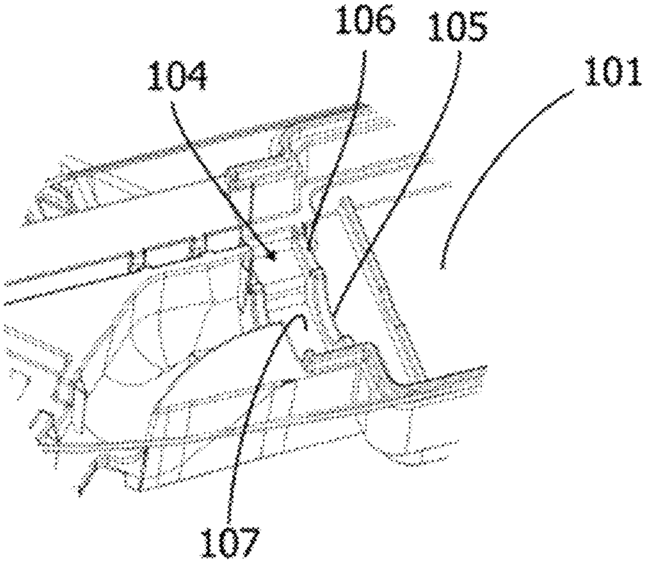
FIG. 8*b* is a detail view of the port of the chamber as indicated by the dashed circle C shown in FIG. 8*a*.
Figure 9B:
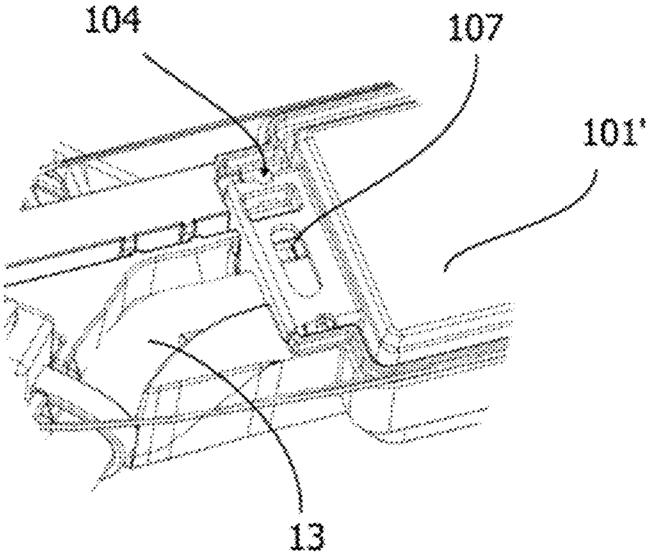
FIG. 9*b* is a detail view of the port of the chamber as indicated by the dashed circle D shown in FIG. 9*a*.
Figure 10B:
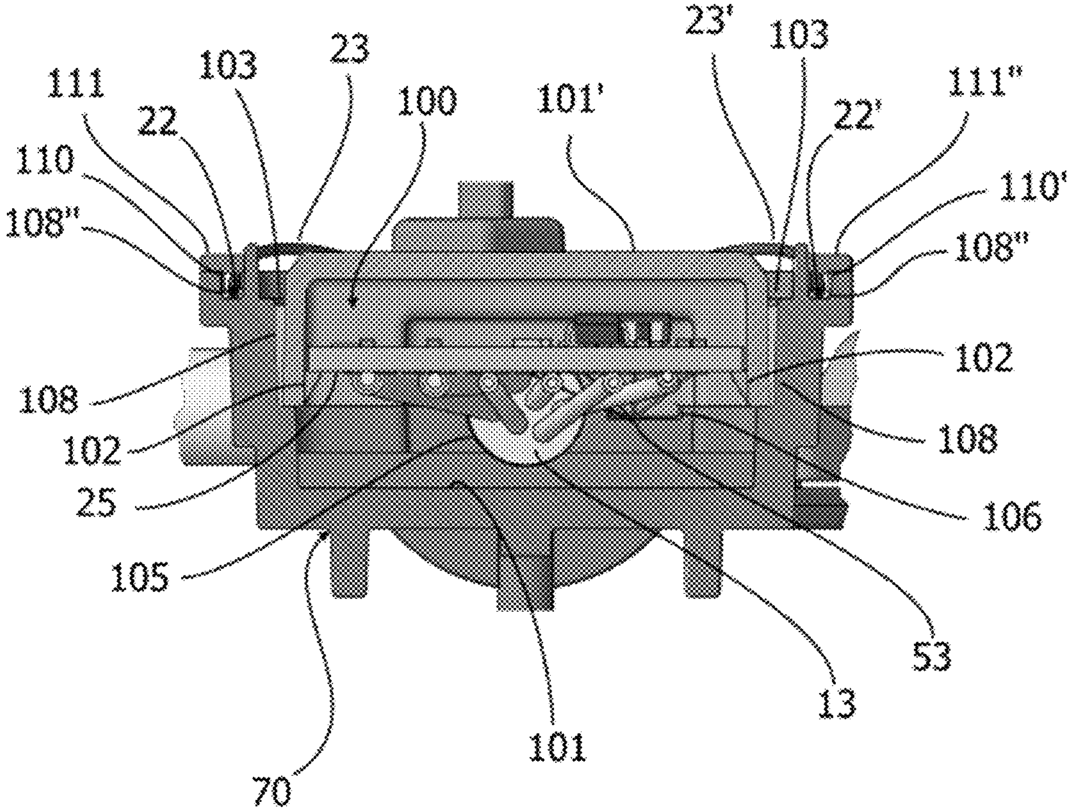
FIG. 10*b* is a cross-sectional view of the liquid-tight chamber along line AA-AA shown in FIG. 4*b*.

The circuit 25 is assembled as follows. The circuit 25 is arranged in the second wall portion 101' so that the circuit 25 rests on a ledge 102 of the second wall portion 101' as shown in FIG. 10*b*. The ledge 102 of the second wall portion 101' can be seen in FIGS. 10*a* and 10*b*. The monitor cable 13 and the imaging cable 53 are arranged at a portion of the monitor cable opening 105 and at a portion of the imaging cable opening 106, respectively, provided by the second wall portion 101'. Then a plurality of wires of the monitor cable 13 and the imaging cable 53 is soldered onto the circuit 25. The second wall portion 101' with the circuit 25 is then placed over the first wall portion 101 so as to enclose the chamber 100 so as to form a wedge-shaped clearance interface 103 (as best seen in FIG. 10*b*) and a port 104 (as best seen in FIGS. 8*b* and 9*b*). The wedge-shaped clearance interface 103 extends between the first and second wall portions 101, 101' and circumferentially around the chamber 100 in a plane perpendicular to the view of FIG. 10*b*. The port 104 includes the monitor cable opening 105 and the imaging cable opening 106 and further an adjacent entrance compartment 107 leading to the openings 105, 106. In order to liquid seal the chamber 100, a first substance in the form of an adhesive, is injected into the entrance compartment 107. As the first substance 108 fills the entrance compartment 107, the first substance 108 flows out of the entrance compartment 107 through the sides thereof and into the wedge-shaped clearance interface 103. The injection continues until the entrance compartment 107 and the wedge-shaped clearance interface 103 are filled with the first substance 108. Alternatively, a second substance 108' may be injected into and fill the entrance compartment 107 and the first substance 108 fills the clearance interface 103. The first substance 108 and/or the second substance 108' may then be cured, e.g. via ultraviolet light, so that the first substance 108 or second substance 108' liquid seals the openings 105, 106 of the liquid-tight port 104 and so that the first substance 108 liquid seals the clearance interface 103 as seen in FIG. 10*b*, whereby the chamber 100 is liquid-sealed.

The steering wires 22, 22' are assembled by threading the steering wires 22, 22' at the bending section (not shown) and then guiding them through respective wire tubes 23, 23' arranged within the insertion tube 30 and the end cap 27. A proximal portion of each wire tube 23, 23' is placed in respective channels 110, 110' that are formed integrally with the frame 70 as best seen in FIG. 10*b*. A third substance 108" is either then injected into the channels 110, 110' or was already present when the wire tubes 23, 23' were placed in the channels 110, 110'. The third substance 108", e.g. an adhesive, is then cured so as to fix the wire tubes 23, 23' in the channels 110, 110 as seen in FIG. 10*b*. The third substance 108" can be cured together with the other substances, e.g. the first substance 108 and/or the second substance 108', or separately. The endoscope handle 20 can then be assembled as follows. The frame 70 including the mounted control device 80, fluid handling device 90, and end cap 27 is arranged in one of the shell parts 60, 60' and the other shell part is placed over to close the shell parts 60, 60'.

During the closure, the columns 61, 61' are arranged in the bearings 71, 71' of the frame 70 abutting the trunnions 85, 85' while allowing the control device 80 to pivot around the pivot axis P. The bearings 71, 71' of the frame 70 are arranged in collars 62, 62' so that the collars 62, 62' retain the bearings 71, 71'.

Furthermore, the alignment pairs are engaged so as to align the columns 61, 61' with respect to each other. In other words, the column axes C, C' are aligned towards coinciding. The corresponding first and second engagement portions engage and fix the frame 70 within the shell parts 60, 60'. A flange 99 of the fluid handling device 90 is arranged in a slit 69 of the first shell part 60', which fixes the fluid handling device 90 relative to the frame 70 (which are fixed via the engagement portions) so that the fluid handling device 90 is locked in a position within the pre-determined path in the range from the proximal end position 93*a* to the distal end position 93*b*. Accordingly, the fluid handling device 90 is adjusted to absorb tolerances of the frame 70 and shell parts 60, 60'.

Lastly, the male snap lock parts 65*a* are snap-locked onto the corresponding female snap lock parts 65*b* to secure the shell parts 60, 60' to each other so as to clamp the trunnions 85, 85' of the control device 80 between the columns 61, 61' of the shell parts 60, 60'. Accordingly, the trunnions 85, 85' are retained between the columns 61, 61'. Since the clamping force experienced by the trunnions 85, 85' substantially coincides with the pivot axis P, as seen in FIG. 5*d*, the pivoting of the control device about the pivot axis P is largely unaffected. The trunnions 85, 85' and the columns 61, 61' are supported by the bearings 71, 71' of the frame 70 so that the control device 80 is rotatable about the pivot axis P. Each trunnion 85, 85' extends partly through the respective bearing 71, 71' and mates with the respective column 61, 61' within the respective bearing 71, 71'. The first shell part 60 comprises a first collar 62, and the second shell part 60' comprises a second collar 62'. The collars 62, 62' each surround the respective column 61, 61' and retain the respective bearings 71, 71' of the frame 70, as best seen in FIG. 5*d*.

Once closed, the shell parts 60, 60' form an exterior surface 68 shaped to form an ergonomic grip for the operator. The exterior surface 68 is divided by a separation line 67 (as seen in FIGS. 5*b* and 5*d*) that extends in a single plane, which is perpendicular to the column axes C, C', as best seen in FIG. 5*d*. The separation line 67 defines the border between the shell parts 60, 60'. The shell parts 60, 60' enclose a cavity 63, which accommodates the frame 70 and the body 84 of the control device 80, while the control lever 81 extends radially relative to the pivot axis P through a first cut-out 68*a* of the exterior surface 68 of the shell parts 60, 60', as shown in FIGS. 3 and 5*a*.

Further, the fluid passage 91 of the fluid handling device 90 extends through the exterior surface 68. The second fluid opening 92' and the third fluid opening 92" of the fluid handling device 90 are arranged exteriorly of the exterior surface 68 and thus accessible for the operator. The first fluid opening 92 of the fluid handling device 90 is arranged within the cavity 63. The fluid connection between the first fluid opening 92 and the working channel tube 34 is protected by the shell parts 60, 60'.

The following items depict examples of embodiments described above.

1. An endoscope handle for an endoscope for visually inspecting inaccessible places, such as human body cavities, the endoscope handle comprising: a frame (70) comprising a first wall portion (101) formed as an integral portion of the frame, the frame being formed as a single component; a liquid-tight chamber (100) accommodating a circuit (25), preferably a printed circuit board, of the endoscope handle, wherein the liquid-tight chamber is at least partly defined by the first wall portion of the frame; and a first shell part (60) and a second shell part (60') together enclosing a cavity (63), the shell parts accommodating and securing the frame within the cavity, the shell parts forming an exterior surface (68) shaped to form an ergonomic grip for an operator, wherein the shell parts and the frame each are formed as separate components.
2. An endoscope handle according to item 1, further comprising a second wall portion (101'), such as a lid, formed separately from the frame, wherein the first wall portion and the second wall portion together enclose the liquid-tight chamber.
3. An endoscope handle according to item 2, wherein an interface (103), such as a clearance interface, between the first wall portion and the second wall portion is liquid-sealed by a first substance (108).
4. An endoscope handle according to any one of the previous items, wherein the liquid-tight chamber comprises a liquid-tight port (104), wherein the endoscope handle comprises one or more cables (13, 53) in communication with the circuit and extending through the liquid-tight port, the one or more cables including: an imaging cable (53) configured for transferring signals and/or power between the circuit and an image sensor of the endoscope, and/or a monitor cable (13) configured for transferring signals and/or power between the circuit and a monitor (11) of an endoscope system.
5. An endoscope handle according to item 4, wherein the liquid-tight port comprises one or more openings (105, 106) in at least one of the first wall portion and the second wall portion, and an entrance compartment (107) leading to the one or more openings, wherein the one or more cables extend through the entrance compartment and through the one or more openings to the circuit, and wherein the entrance compartment comprises a second substance (108'), such as a second sealant, providing a seal around the one or more cables so as to liquid-seal the one more openings of the liquid-tight port, wherein the entrance compartment is preferably integrally formed with the frame.
6. An endoscope handle according to any one of the previous items further comprising a control device (80) comprising a control lever (81) for being manipulated by an operator, wherein the control device is at least partly accommodated in the cavity (63) and is secured to the frame, the control device being configured for, upon manipulating the control lever, steering a distal end (50) of the endoscope by pivoting about a pivot axis (P), wherein the frame comprises at least one channel (110, 110') configured for accommodating a respective wire tube (23, 23') housing a steering wire (22, 22') of the endoscope.
7. An endoscope for visually inspecting inaccessible places, the endoscope comprising: the endoscope handle (20) according to any one of the previous items; a distal tip part (50) including an image sensor positioned in an interior cavity of the distal tip part; and an insertion tube (30) for insertion into a patient and extending between the endoscope handle and the distal tip part; wherein the image sensor being in signal communication with the circuit (25) of the endoscope handle preferably via an imaging cable (53) through the insertion tube.
8. An endoscope according to item 7, wherein the endoscope comprises: a bending section (40) including articulated segments (41) connected via hinges (42), the bending section being attached to the distal tip part and the insertion tube; and at least one steering wire (22, 22') attached to a body (84) of the control device of the endoscope handle and running through a dedicated wire tube (23, 23') in the insertion cord to the bending section so that manipulating the control device by an operator tensions the at least one steering wire (22) and effects bending of the bending section (40) so as to steer the distal end tip of the endoscope.
9. An endoscope according to item 8, wherein each wire tube (23, 23') is accommodated in a respective channel (110, 110') formed integrally with the frame, wherein each channel comprises a third substance (108"), such as a cured adhesive, fixing the respective wire tube to the channel.
10. An endoscope according to any one of items 8-9, wherein the at least one steering wire includes a first steering wire (22) and a second steering wire (22'), wherein the frame comprises a first channel (110) and a second channel (110'), the channels (110, 110') being formed integrally with the frame, wherein the first and second channel extend on opposite sides of the frame, preferably on opposite sides of the liquid-tight chamber, and along a longitudinal axis (L) of the frame.
11. An endoscope system for visually inspecting inaccessible places, such as human body cavities, the endoscope system comprising: a monitor (11), and an endoscope (1) comprising endoscope handle (20) according to any one of items 1-6 or an endoscope (1) according to any one of items 7-10, wherein the endoscope is connectable to the monitor, preferably via a monitor cable (13), and the monitor is configured for displaying an image captured by the image sensor of the distal tip part.
12. A method of assembling an endoscope handle (20), comprising: providing: a frame (70) comprising a first wall portion (101) formed as an integral portion of the frame, the frame being formed as a single component, and a first shell part (60) and a second shell part (61'); arranging the frame in one of the shell parts; arranging a circuit (25), preferably a printed circuit board, at the first wall portion, and liquid sealing the first wall portion to form a liquid-tight chamber (100) defined at least partly by the first wall portion; and closing the first shell part and the second shell part to enclose a cavity (63) and accommodating and securing the frame within the cavity and forming an exterior surface (68) shaped to form an ergonomic grip for an operator.
13. A method according to item 12, wherein said providing further comprises: providing a second wall portion (101'), such as a lid, formed separately from the frame; wherein the step of liquid-sealing the first wall portion further comprises: arranging the second wall portion adjacent to the first wall portion to form an interface (103) between the first wall portion and the second wall portion, and applying a first substance (108) to liquid-seal the interface between first wall portion and the second wall portion, whereby the first wall portion and the second wall portion define the liquid-tight chamber.

14. A method according to items 12-13, further comprising: inserting one or more cables (53, 13), such as an imaging cable (53) and/or a monitor cable (13), in communication with the circuit through a port (104) of the chamber, preferably through one or more openings, such as an imaging cable opening (106) and/or a monitor cable opening (105), formed in the first wall portion and/or the second wall portion; filling an entrance compartment (107) of the port with a second substance (108'), such as a second sealant, so that the second substance envelops the one or more cables in the entrance compartment; and causing the second substance to or letting the second substance liquid-seal the port, such as by curing the second adhesive, for instance by ultraviolet light, or by letting the second adhesive cure.

15. A method according to items 12-14 for assembling an endoscope (1), the endoscope comprising the endoscope handle (20), the method further comprising: arranging one or more wire tubes (23, 23') each in a respective channel (110, 110') formed integrally with the frame, each of the one or more wire tubes accommodating a dedicated steering wire (22, 22') that, when tensioned, effects bending of a bending section (40) so as to steer a distal end tip (50) of the endoscope (1); applying a third substance (108") in each channel; and causing or letting the third substance cure so as to fix each wire tube in the respective channel.

LIST OF REFERENCES

1 endoscope
11 monitor
12 cable socket
13 monitor cable
20 handle
22 steering wire
23 wire tube
24 wire crimp
25 circuit
27 end cap
30 insertion tube
31 proximal end
32 distal end
34 working channel tube
35 proximal opening
40 bending section
41 bending segment
42 hinge
50 distal tip part
53 imaging cable
60 shell part
61 column
62 collar
63 cavity
64*a* first alignment part
64*b* second alignment part
65*a* male snap lock part
65*b* female snap lock part
66 second engagement portion
67 separation line
68 exterior surface
68*a* cut out
69 slit
70 frame
71 bearing
72 arm
73 proximal longitudinal end
74 distal longitudinal end
75 first tube guide passage
76 first engagement portion
77 ramp
78 pin
78*a* pin head
78*b* pin body
80 control device
81 control lever
83 friction-inducing surface
84 body
85 trunnion
86 wire loop portion
90 fluid handling device
91 fluid passage
92 fluid opening
93 slot
93*a* proximal end position
93*b* distal end position
93*c* distance
95 second tube guide passage
96 gap
99 flange
100 chamber
10 wall portion
102 ledge
103 interface
104 port
105 monitor cable opening
106 imaging cable opening
107 entrance compartment
108 sealant
110 channel
111 retaining member
P pivot axis
C column axis
L longitudinal axis

We claim:

1. An endoscope comprising:

an image sensor;

one or more cables;

a circuit;

a steering actuator including trunnions, the steering actuator being rotatable about a pivot axis extending through the trunnions;

wire tubes comprising a first wire tube and a second wire tube;

steering wires configured to steer a distal end of the endoscope, the steering wires comprising a first steering wire extending from the steering actuator to and through the first wire tube and a second steering wire extending from the steering actuator to and through the second wire tube;

a bending section;

an insertion tube between the bending section and a handle, the wire tubes and the steering wires extending through the insertion tube; and the handle attached to the insertion tube and including:

a frame comprising a single component including, as integral portions of the frame, a proximal end and a distal end, bearings at the proximal end, and a first wall portion between the proximal end and the distal end, the bearings receiving the trunnions and rotatably supporting the steering actuator;

a second wall portion formed separately from the frame;

a liquid-tight chamber accommodating the circuit, the liquid-tight chamber being at least partly defined by the first wall portion of the frame and the second wall portion, the liquid-tight chamber comprising a liquid-tight port, the one or more cables being connected to the circuit and extending through the liquid-tight port, the first wall portion comprising a proximal wall and a distal wall opposite the proximal wall, and the wire tubes extending longitudinally along opposite sides of the frame and proximally of the distal wall; and a first shell part and a second shell part together enclosing a cavity and accommodating the frame within the cavity, wherein the first shell part and the second shell part and the frame each are formed as separate components.

2. The endoscope of claim 1, wherein the second wall portion comprises a lid of the liquid-tight chamber.

3. The endoscope of claim 1, wherein an interface between the first wall portion and the second wall portion is liquid-sealed by a first substance.

4. The endoscope of claim 3, wherein the interface is a clearance interface.

5. The endoscope of claim 1, wherein the one or more cables include:

an imaging cable to transfer signals and/or power between the circuit and the image sensor, and/or a monitor cable adapted to transfer signals and/or power between the circuit and a monitor.

6. The endoscope of claim 1, wherein the liquid-tight port comprises one or more openings in at least one of the first wall portion and the second wall portion, an entrance compartment leading to the one or more openings, wherein the one or more cables extend through the entrance compartment and through the one or more openings to the circuit, and wherein the entrance compartment comprises a second substance providing a seal around the one or more cables so as to liquid-seal the one more openings of the liquid-tight port.

7. The endoscope of claim 6, wherein the entrance compartment is integrally formed with the frame.

8. The endoscope of claim 1, the endoscope further comprising:

a distal tip part housing the image sensor;

wherein the bending section includes segments connected via hinges, the bending section being attached to and between the distal tip part and the insertion tube, wherein the one or more cables include an image cable connecting the image sensor and the circuit; and wherein the steering wires are attached to a body of the steering actuator.

9. The endoscope of claim 1, wherein the frame further comprises a main wall, a first channel accommodating the first wire tube and a second channel accommodating the second wire tube, wherein the main wall forms a base of the liquid-tight chamber, the base being surrounded by the first wall portion and facing the second wall portion, and wherein the first channel and the second channel are formed integrally with the frame.

10. The endoscope of claim 9, wherein the first channel comprises a third substance fixing the first wire tube to the first channel, and wherein the second channel comprises the third substance fixing the second wire tube to the second channel.

11. The endoscope of claim 10, wherein the third substance comprises a cured adhesive.

12. The endoscope of claim 10, wherein the first channel and the second channel extend longitudinally on the opposite sides of the frame.

13. The endoscope of claim 9, wherein the first channel and the second channel extend longitudinally on opposite sides of the liquid-tight chamber.

14. The endoscope of claim 1, wherein the first wall portion comprises longitudinal walls connecting the proximal wall and the distal wall, and channels formed adjacent the longitudinal walls, wherein the wire tubes are adhesively bonded in the channels.

15. The endoscope of claim 1, wherein the first trunnion extends from a first side and the second trunnion extends from a second side of a body of the steering actuator, wherein the first wall portion further comprises longitudinal walls connecting the proximal wall and the distal wall, and wherein a rotation plane of the body of the steering actuator passes between the first side and the second side and traverses the first wall portion.

16. The endoscope of claim 15, wherein the frame forms a base of the liquid-tight chamber, the base being surrounded by the first wall portion and facing the second wall portion, wherein the base is on a first side of the rotation plane, and wherein the second wall portion is on a second side of the rotation plane.

17. The endoscope of claim 15, the steering wires extend along the longitudinal walls of the first wall portion on a second side of the rotation plane.

18. The endoscope of claim 1, wherein the first trunnion extends from a first side and the second trunnion extends from a second side of a body of the steering actuator, wherein a rotation plane of the body of the steering actuator passes between the first side and the second side, wherein the frame comprises a main wall, the main wall providing a base of the liquid-tight chamber, and wherein the first wall portion protrudes orthogonally from the main wall and through the rotation plane.

19. The endoscope of claim 1, wherein the first trunnion extends from a first side and the second trunnion extends from a second side of a body of the steering actuator, wherein a rotation plane of the body of the steering actuator passes between the first side and the second side and traverses the first wall portion, wherein the frame forms a base of the liquid-tight chamber, the base being surrounded by the first wall portion and facing the second wall portion, wherein the base is on a first side of the rotation plane, and wherein the second wall portion is on a second side of the rotation plane.

20. The endoscope of claim 1, wherein the frame comprises a first channel and a second channel formed integrally with the frame, wherein the first wire tube is adhesively bonded to the first channel, and wherein the second wire tube is adhesively bonded to the second channel.

21. The endoscope of claim 1, wherein the frame comprises a main wall, a support wall, and parallel arms at the proximal end of the frame, wherein the support wall protrudes orthogonally from the main wall and extends longitudinally between the arms and the proximal wall, and wherein the arms comprise the bearings.

22. The endoscope of claim 1, wherein the first shell part and the second shell part are attached at a seam, the seam comprising an aperture, and the steering actuator comprising a control lever extending outwardly through the aperture at the seam.

23. An endoscope system comprising:

a monitor; and the endoscope of claim 1, wherein the endoscope is connectable to the monitor, and the monitor is configured to display an image captured by the image sensor.

24. A method of assembling the endoscope of claim 1, the method comprising:

arranging the frame in the first shell part or the second shell part;

arranging the circuit at the first wall portion;

liquid sealing the first wall portion to form the liquid-tight chamber; and closing the first shell part and the second shell part to enclose the cavity and accommodate and secure the frame within the cavity.

25. The method of claim 24, the method further comprising arranging the second wall portion adjacent to the first wall portion to form an interface between the first wall portion and the second wall portion; and applying a first substance to liquid-seal the interface between first wall portion and the second wall portion.

26. The method of claim 25, further comprising inserting the one or more cables through the liquid-tight port of the liquid-tight chamber; adding a second substance to an entrance compartment of the liquid-tight port so that the second substance envelops the one or more cables in the entrance compartment; and causing the second substance to or letting the second substance liquid-seal the liquid-tight port.

27. The method of claim 26, wherein the frame comprises a first channel and a second channel formed integrally with the frame and extending on the opposite sides of the frame, the method further comprising arranging the first wire tube in the first channel and the second wire tube in the second channel, the first wire tube accommodating the first steering wire, and the second wire tube accommodating the second steering wire; applying a third substance in the first channel and in the second channel; and causing or letting the third substance cure so as to fix the first wire tube in the first channel and the second wire tube in the second channel.

* * * * *